(12) United States Patent
Kay

(10) Patent No.: US 10,039,903 B2
(45) Date of Patent: Aug. 7, 2018

(54) WIRE GUIDE AND METHOD OF MAKING THE SAME

(71) Applicant: Cook Medical Technologies LLC, Bloomington, IN (US)

(72) Inventor: Thomas Albert Kay, Bloomington, IN (US)

(73) Assignee: COOK MEDICAL TECHNOLOGY LLC, Bloomington, IN (US)

( * ) Notice: Subject to any disclaimer, the term of this patent is extended or adjusted under 35 U.S.C. 154(b) by 359 days.

(21) Appl. No.: 14/138,773

(22) Filed: Dec. 23, 2013

(65) Prior Publication Data

US 2014/0188005 A1    Jul. 3, 2014

Related U.S. Application Data

(60) Provisional application No. 61/746,504, filed on Dec. 27, 2012.

(51) Int. Cl.
*A61M 25/09* (2006.01)

(52) U.S. Cl.
CPC ... *A61M 25/09* (2013.01); *A61M 2025/09108* (2013.01); *A61M 2025/09133* (2013.01); *Y10T 29/49826* (2015.01)

(58) Field of Classification Search
CPC ........ A61M 25/09; A61M 2025/09108; A61M 2025/09133; A61M 2025/09091; A61M 2025/0915; A61M 525/0054
See application file for complete search history.

(56) References Cited

U.S. PATENT DOCUMENTS

| | | | |
|---|---|---|---|
| 4,953,553 A | 9/1990 | Tremulis | |
| 4,966,163 A | 10/1990 | Kraus et al. | |
| 5,836,893 A | 11/1998 | Urick | |
| 6,001,068 A | 12/1999 | Uchino et al. | |
| 6,017,319 A * | 1/2000 | Jacobsen | A61M 25/09 600/585 |
| 6,203,485 B1 | 3/2001 | Urick | |
| 6,488,637 B1 | 12/2002 | Eder et al. | |
| 6,866,642 B2 * | 3/2005 | Kellerman | A61M 25/09 600/585 |
| 7,074,197 B2 * | 7/2006 | Reynolds | A61M 25/09 600/585 |
| 7,153,277 B2 | 12/2006 | Skujins et al. | |
| 7,717,864 B1 | 5/2010 | Grandfield et al. | |
| 7,747,314 B2 | 6/2010 | Parins et al. | |

(Continued)

FOREIGN PATENT DOCUMENTS

JP    4-009162    1/1992

*Primary Examiner* — Daniel Cerioni
*Assistant Examiner* — Yasmeen S Warsi
(74) *Attorney, Agent, or Firm* — Brinks Gilson & Lione

(57) ABSTRACT

A wire guide and methods for making the same is provided. The method includes joining a proximal core wire comprised of a stiff material to a distal core wire comprised of a highly elastic wire material. The proximal core wire may have a recess at a distal face and the distal core wire is secured within the recess. The recess may be machined into the distal face of the proximal core wire. The distal core wire may be a coaxial wire having a sleeve of material that is easily weldable to the proximal core wire. The sleeve is welded to the proximal core wire and a distal portion of the sleeve is then removed to expose the distal core wire.

14 Claims, 4 Drawing Sheets

(56) References Cited

U.S. PATENT DOCUMENTS

| | | |
|---|---|---|
| 7,758,520 B2 | 7/2010 | Griffin et al. |
| 2007/0208218 A1* | 9/2007 | Haller .................. A61M 25/09 |
| | | 600/104 |
| 2008/0200839 A1* | 8/2008 | Bunch .................. A61M 25/09 |
| | | 600/585 |
| 2011/0071435 A1 | 3/2011 | Shamay et al. |
| 2011/0118628 A1 | 5/2011 | Zhou et al. |
| 2011/0306949 A1* | 12/2011 | Specht .................. A61M 25/09 |
| | | 604/528 |

\* cited by examiner

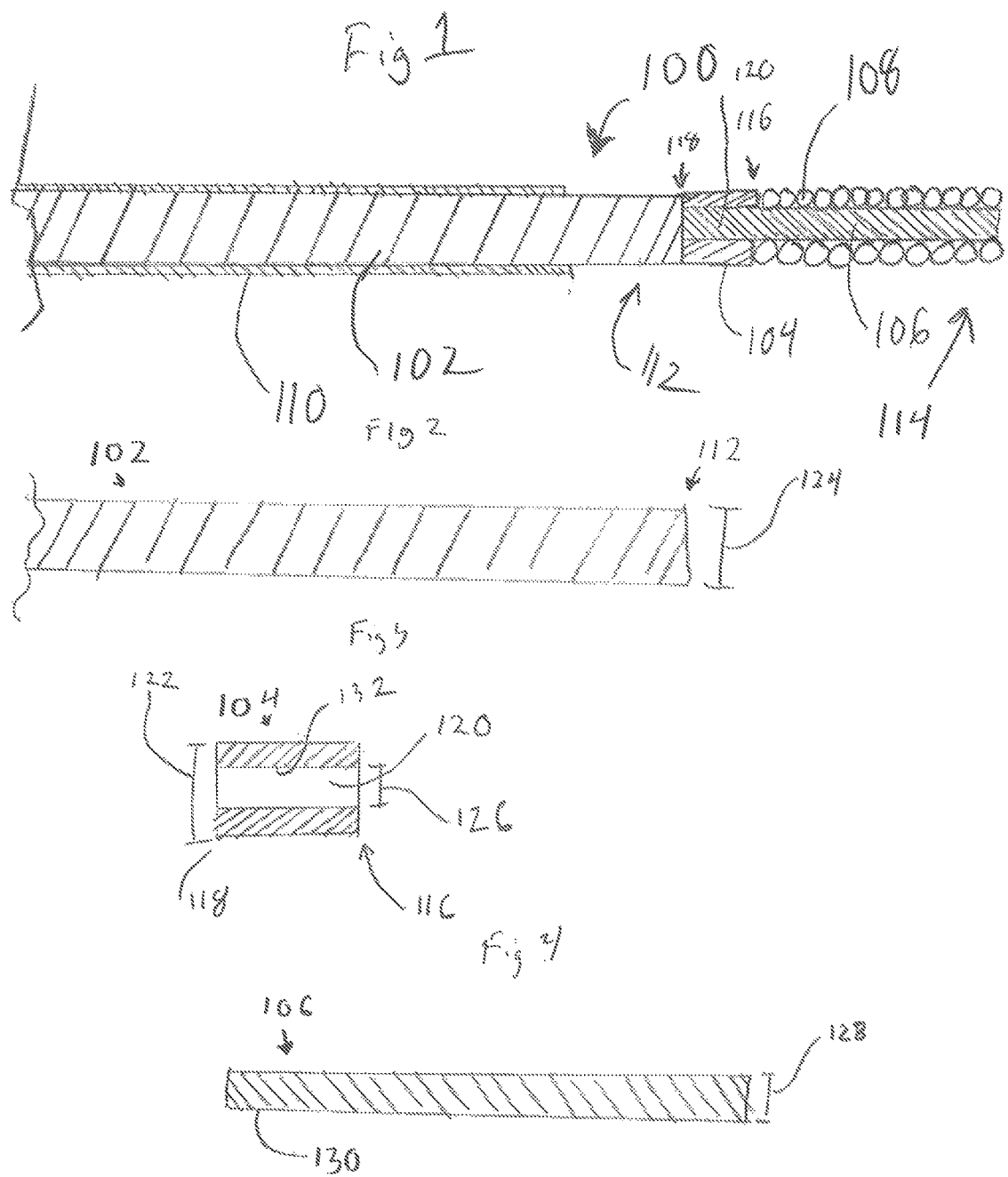

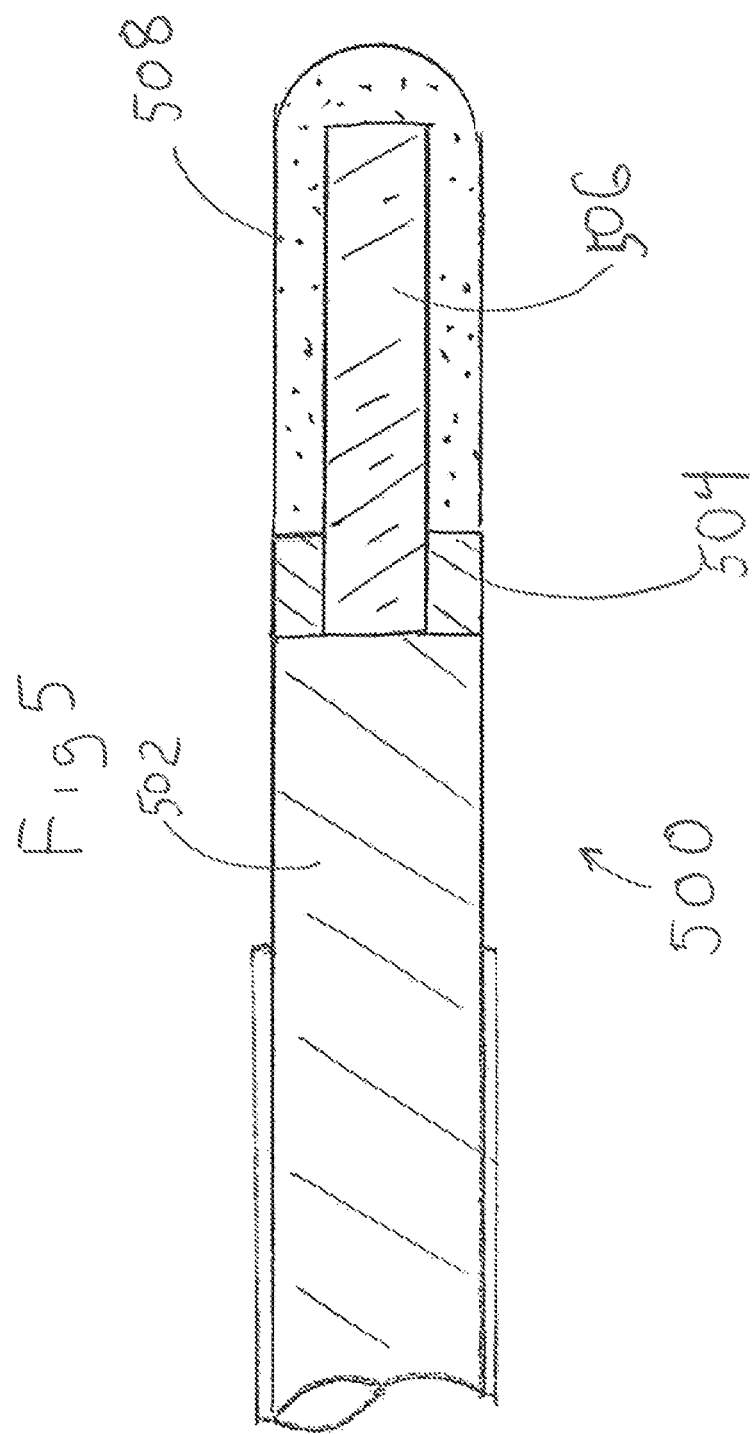

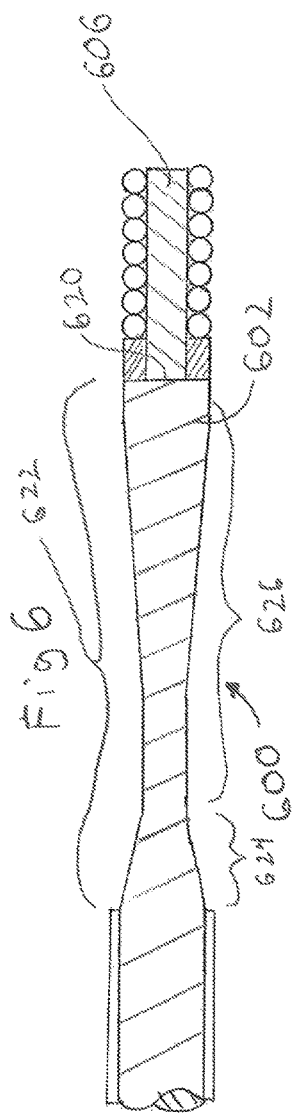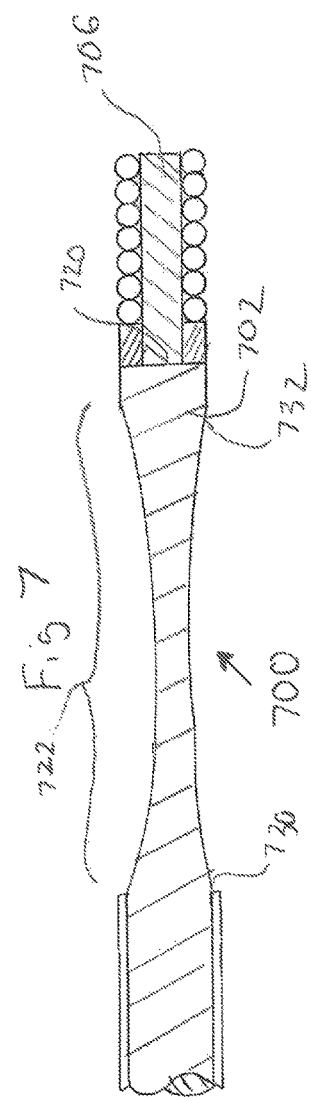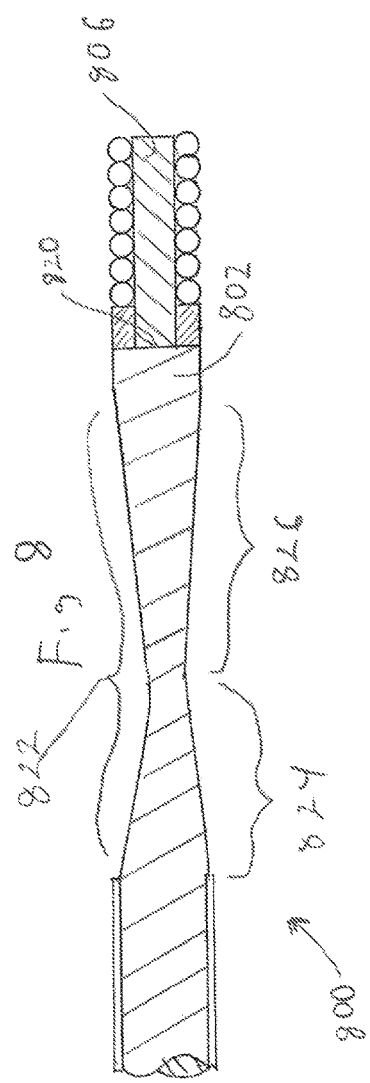

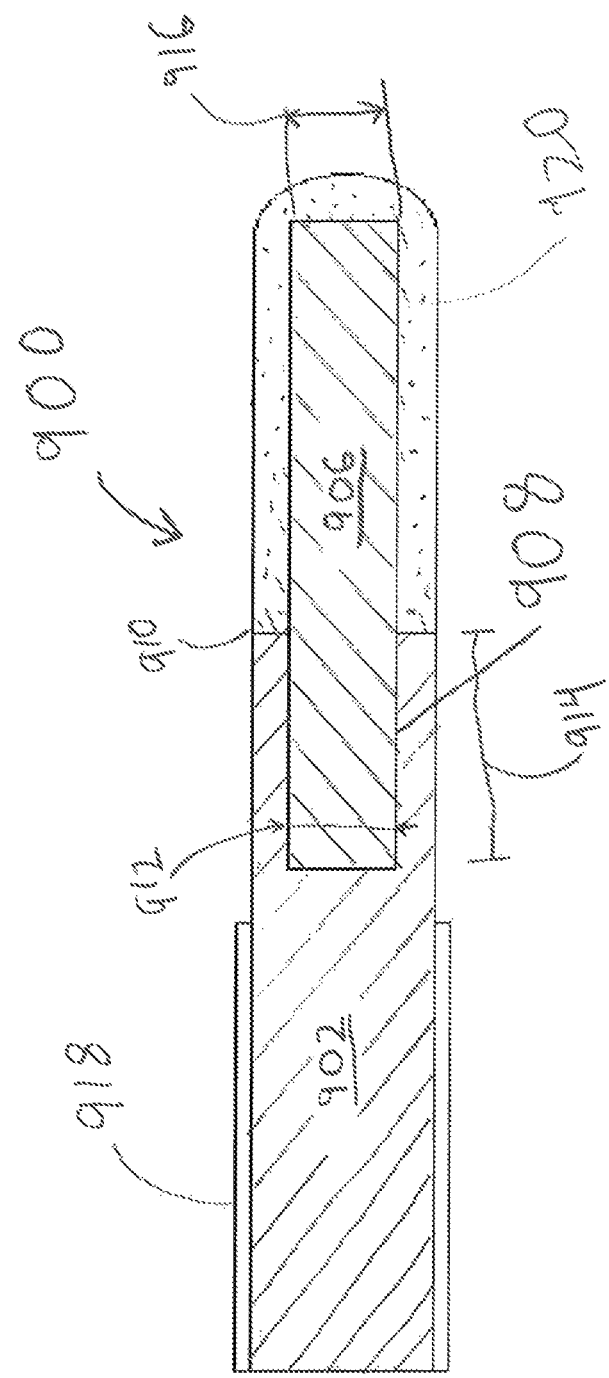

WIRE GUIDE AND METHOD OF MAKING THE SAME

BACKGROUND

1. Field

Embodiments of the present invention relate to medical devices and more particularly, embodiments relate to wire guides and methods for making wire guides.

2. Background

Wire guides are used to gain access to specific inner areas of the body. The wire guide may enter the body through a small opening and travel to parts of the body through body channels. For example, wire guides may be passed through the body via peripheral blood vessels, gastrointestinal tract, or the urinary tract. Wire guides are commercially available and are currently used in cardiology, gastroenterology, urology, and radiology. Once in place at a desired location in the body, wire guides are commonly used as guides for the introduction of additional medical instruments, e.g., catheters.

One design challenge for wire guides is that they need to have sufficient stiffness for a surgeon to push the wire guide through a patient's body lumen while at the same time having enough flexibility at the distal end to avoid damaging the body lumen or plastically deforming Improved strength and enhanced flexibility, however, are two properties which for the most part are diametrically opposed to one another. That is, an increase in one of these properties usually involves a decrease in the other. Accordingly, further improvements and enhancements in the strength and flexibility of wire guides may be desirable.

BRIEF SUMMARY

Embodiment of the invention includes a method for making a wire guide. In the method a proximal core wire comprised of a first material having a high modulus of elasticity, the proximal core wire having a distal end, a distal face, and a first longitudinal axis is obtains. Then a coaxial wire comprised of a core material having a low modulus of elasticity and a sleeve material disposed about the core material, the sleeve material being weldable to the first material, the coaxial wire having a proximal end, a proximal face, and a second longitudinal axis is obtained. The first longitudinal axis is aligned with the second longitudinal axis. The first material is joined to the sleeve material at the distal face of the proximal core wire and the proximal face of the coaxial wire. Then a distal portion of the sleeve material is removed to expose the core material.

Another embodiment of the invention includes another method for making a wire guide. In the method a proximal core wire comprised of a first material having a high modulus of elasticity is obtained. The proximal core wire has a distal end, a distal face, a first outside diameter, and a first longitudinal axis. A distal core wire comprised of a second material having a low modulus of elasticity is obtained. The distal core wire has a proximal end, a proximal face, a second outside diameter, and a second longitudinal axis. Material from the distal face of the proximal core wire is removed to form a cylindrical recess having an inside diameter complementary to the second outside diameter. The first longitudinal axis is aligned with the second longitudinal axis and the proximal end of the distal core wire is inserted into the recess. The proximal end of the distal core wire is then secured within the recess.

Another embodiment of the invention is directed to a wire guide. The wire guide has a proximal core wire comprised of a first material having a high modulus of elasticity. The proximal core wire has a distal end and a first axis. A distal core wire is comprised of a second material having a low modulus of elasticity. The distal core wire has a distal core wire length, a proximal end, a second axis, an outer surface, and an outer diameter. The second axis and the first axis are coaxial. A sleeve is secured about the proximal end of the distal core wire, the sleeve having a sleeve length less than the distal core wire length, an inner surface and a second outer diameter, the inner surface facing the outer surface of the distal core wire, the second diameter matching the first outer diameter, and the sleeve being joined to the distal end of the proximal core wire.

Another embodiment is directed to wire guide having a proximal core wire and a distal core wire. The proximal core wire is comprised of a first material having a high modulus of elasticity. The proximal core wire has a distal end, a cylindrical recess disposed at the distal end, and a first axis. The cylindrical recess has a recess inner surface. The distal core wire is comprised of a second material having a low modulus of elasticity. The distal core wire has a proximal end, a second axis, and an outer surface. The proximal end is secured within the cylindrical recess with the recess inner surface facing the outer surface.

BRIEF DESCRIPTION OF THE DRAWINGS

To further clarify the above and other advantages and features of the one or more present inventions, reference to specific embodiments thereof are illustrated in the appended drawings. The drawings depict only typical embodiments and are therefore not to be considered limiting. One or more embodiments will be described and explained with additional specificity and detail through the use of the accompanying drawings in which:

FIG. 1 illustrates an embodiment of a wire guide.
FIG. 2 illustrates a proximal segment of the wire guide of FIG. 1.
FIG. 3 illustrates a sleeve segment of the wire guide of FIG. 1.
FIG. 4 illustrates a distal segment of the wire guide of FIG. 1.
FIG. 5 illustrates another embodiment of a wire guide.
FIG. 6 illustrates another embodiment of a wire guide.
FIG. 7 illustrates another embodiment of a wire guide.
FIG. 8 illustrates another embodiment of a wire guide.
FIG. 9 illustrates another embodiment of a wire guide.
The drawings are not necessarily to scale.

DETAILED DESCRIPTION

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Embodiments of the present invention will now be further described. In the following passages, different aspects of the embodiments are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Embodiments of the present invention seek to overcome some of the concerns associated with providing a wire guide for guiding various medical devices through a body channel or cavity of a patient while providing sufficient stiffness and flexibility to the wire guide so that the wire guide can be pushed through the patients' body without kinking and causing damage to the surrounding body tissue.

Additional advantages of the present invention will become readily apparent from the following discussion, particularly when taken together with the accompanying drawings.

In the following discussion, the terms "proximal" and "distal" will be used to describe the opposing axial ends of the inventive self-expanding cell collection device, as well as the axial ends of various component features. The term "proximal" is used in its conventional sense to refer to the end of the wire guide (or component thereof) that is closest to the operator during use of the wire guide. The term "distal" is used in its conventional sense to refer to the end of the wire guide (or component thereof) that is initially inserted into the patient, or that is closest to the patient during use. For example, a wire guide may have a proximal end and a distal end, with the proximal end designating the end closest to the operator, and the distal end designating an opposite end of the wire guide. Similarly, the term "proximally" refers to a direction that is generally towards the operator along the path of the wire guide and the term "distally" refers to a direction that is generally away from the operator along the wire guide.

FIG. 1 illustrates a cross section of an embodiment of a wire guide 100 according to the present invention. The wire guide 100 has a proximal end (not shown) and a distal end 114. The wire guide 100 comprises a proximal core wire 102, a sleeve 104, and a distal core wire 106. The proximal core wire 102 and the distal core wire 106 may be made by any suitable wire forming process known to those skilled in the art, such as pultrusion or extrusion of a metal alloy through a mold or die that has a circular opening.

FIG. 2 through FIG. 4 illustrate cross sections of the proximal core wire 102, the sleeve 104, and the distal core wire 106 individually for clarity. The following description is in reference to FIG. 1 through FIG. 4. In some embodiments, the wire guide 100 further comprises additional features such as a radiopaque marker 108 and/or a lubricated sleeve 110 as shown in FIG. 1.

The proximal core wire 102 has a proximal end (not shown) and a distal face 112. The proximal end extends out of a patient's body and is manipulated by a surgeon to guide the distal end 114 of the wire guide through a body lumen. The proximal core wire 102 is comprised of a material having good pushability. One example of a suitable material is a material having a high modulus of elasticity such as stainless steel.

The sleeve 104 has a distal end 116 and a proximal face 118. A lumen 120 is disposed in a longitudinal orientation within the sleeve 104. The proximal face 118 of the sleeve 104 is joined to the distal face 112 of the proximal core wire 102 as shown in FIG. 1. The proximal core wire 102 may be joined to the sleeve 104 by known techniques such as welding, adhesives, or other techniques as known in the art. Welding may include friction welding, ultrasonic welding, laser welding, and resistance welding.

The sleeve 104 has an outside diameter 122 that may be substantially the same as an outside diameter 124 of the proximal core wire 102. In some embodiments the outside diameter 122 of the sleeve 104 may be greater than the outside diameter 124 of the proximal core wire 104. In other embodiments, the sleeve 104 may have an outside diameter 122 that is less that the outside diameter 124 of the proximal core wire 104. The sleeve 104 may be modified at the proximal face 118 to assist in the joining of the sleeve 104 to the proximal core wire 102. For example, the proximal face 118 of the sleeve 104 may be modified with a beveled edge to enhance welding of the sleeve 104 to the proximal core wire 102. The bore 120 disposed within the sleeve 104 runs longitudinally. The bore 120 has an inside diameter 126 that is less than then outside diameter 124 of the proximal core wire 102. In some embodiments, the sleeve 104 comprises a stainless steel material. In another embodiment the sleeve 104 comprises a material that exhibits good weldability to stainless steel such as nickel.

The distal core wire 106 is comprised of a material that has enhanced flexibility and kink resistance. Suitable materials have a relatively low modulus of elasticity compared to the proximal core wire 102. One example of a suitable material is a nickel titanium alloy such as Nitinol. The distal core wire 106 has an outside diameter 128 that complements the inside diameter 126 of the bore 120. Thus the distal core wire 106 may be inserted into the bore 120 and an outside surface 130 of the distal core wire 106 would face an inside surface 132 of the bore 120.

The distal core wire 106 is secured within the bore 120 such that when the sleeve 104 is joined to the proximal core wire 102, the distal core wire 104 is secured to the proximal core wire 104 as well. The distal core wire 106 may be secured within the bore 120 using a commonly available technique such as a press fit, an interference fit, an adhesive, a solder, swaging, or other technique. In some embodiments the sleeve 104 may be heated prior to inserting the distal core wire 106 in the bore 120. The heating causes the bore 120 to expand, facilitating insertion of the distal core wire 106. When the sleeve 104 cools, the bore 120 shrinks, further securing the distal core wire 106. In other embodiment the distal core wire 106 may be cooled prior to insertion. Cooling the distal core wire 106 causes it to shrink, facilitating insertion of the distal core wire 106 in the bore 120.

In some embodiments, the distal core wire 106 and sleeve 104 are provided as a preformed component with the distal core wire 106 covered by the sleeve 104 extending the entire length distal core wire 106. The sleeve 104 of the preformed component is then machined to expose the distal core wire 106 along a distal portion of the preformed component. For example, a coaxial wire having an inner core forming the distal core wire 106 and an outer sleeve forming the sleeve 104 may be manufactured during a wire forming process. The coaxial wire then has the sleeve 104 removed along a distal portion to expose the inner core.

Returning to FIG. 1, the portion of the distal core wire 106 extending from the sleeve 104 may be covered by a radiopaque material. In FIG. 1, the radiopaque material may comprise a coil 108 wound around the distal core wire 106. The coil 108 is comprised of a radiopaque material such as platinum or a platinum alloy. The coil 108 may be bonded to the distal core wire 106 or in some embodiments may be over molded by a plastic material.

A lubricating coating 110 may be applied to the wire guide 100 to reduce friction and ease the movement of the wire guide 100 through a body lumen. In some embodiments the lubricating coating 110 comprises a hydrophilic material. In other embodiment, the lubricating coating 100 comprises polytetrafluoroethylene material.

FIG. 5 illustrates a wire guide 500 similar to the wire guide 100 of FIG. 1. The wire guide 500 is comprised of a proximal core wire 502, a distal core wire 506, and a sleeve 504. However, in place of the coil 108 of the embodiment of FIG. 1, the embodiment of FIG. 5 has a radiopaque jacket 508 covering a distal end of distal core wire 506. The radiopaque jacket 508 may comprise a plastic over molding having a radiopaque material, such as barium, compounded within the plastic.

FIG. 6 illustrates an optional configuration of a proximal core wire 602 for use in a wire guide 600. Because the proximal core wire 602 is much stiffer than a distal core wire 606, the transition from the proximal core wire 602 to the distal core wire 606 may result in a stress concentration at an interface 620 during flex or torsion. To reduce the stress concentration at the interface 620, the proximal core wire 602 has a tapered section 622 where an outside diameter of the proximal core wire 602 is reduced. The reduction in the diameter of the proximal core wire 602 reduces the stiffness of the proximal core wire 602 so the transition from the stiffness of the proximal core wire 602 to the stiffness of the distal core wire 606 is not as abrupt as it would be otherwise. The taper of tapered section 622 is general a straight taper tapering inward at a first tapered section 624 and tapering outward at a second tapered section 626. The first tapered section 624 is shorter in length and sharper than the second tapered section 626.

FIG. 7 illustration another optional configuration of a proximal core wire 702 for use in a wire guide 700. The proximal core wire 702 has a tapered section 722 reducing the stress at an interface 720 between the proximal core wire 702 and the distal core wire 706. In contrast to the tapered section 622 of the embodiment of FIG. 6, the embodiment of FIG. 7 has a curved taper that curves from an inward taper at a proximal taper end 730 and outward at a distal tapered end 732.

FIG. 8 illustrates another optional configuration of a proximal core wire 802 for use in a wire guide 800. The proximal core wire 802 has a tapered section 822 reducing the stress at an interface 820 between the proximal core wire 802 and the distal core wire 806. This tapered section 822 is similar to the tapered section 626 of FIG. 6 and has a first inwardly tapered section 824 and a second outwardly tapering section 826. The first inward tapering section 824 has a generally straight inward taper and the second outward tapering section 826 has a generally straight outward taper. In contrast to the embodiment of FIG. 6, the first inward tapered section 824 is about the same length as the second outward tapered section 826. The profiles of the tapered sections shown in FIG. 6 through FIG. 8 are exemplary and embodiments of the invention are not limited to these examples.

FIG. 9 illustrates another embodiment of a wire guide 900. The wire guide 900 of FIG. 9 is similar to the wire guide 500 of FIG. 5 and is comprised of a proximal core wire 902 and a distal core wire 906. The proximal core wire 902 has a recess 908 disposed in the distal end 910. The recess 908 may be cylindrical and in the embodiment of FIG. 9, the recess 908 has an inside diameter 912 and a depth 914. The distal core wire 906 has an outside diameter 916 complementary to the inside diameter 912. In other embodiments the recesses 908 may be tapered and the distal core wire 906 may have a complementary taper. The distal core wire 906 is secured within the recess 908 using techniques as known in the art such as a swage, a press fit, a crimp, adhesives, weld, and combinations thereof. The recess 908 may be formed in the proximal core wire 902 using a conventional machining technique such as electrical discharge machining (EDM). The proximal core wire may have a tapered profile like that shown in FIG. 6 through FIG. 8 to reduce stress at the transition from the proximal core wire 902 to the distal core wire 906. The wire guide 900 may optionally be fitted with a lubricating coating 918 and a radiopaque marker tip 920.

Embodiments of the invention include a process for manufacturing a wire guide. In the process a proximal core wire and a coaxial wire are obtained. The proximal core wire is comprised of a first material having a high modulus of elasticity and has a distal end, a distal face, and a first longitudinal axis. The coaxial wire is comprised of a core material having a low modulus of elasticity and a sleeve material disposed about the core material. The sleeve material is weldable to the first material. The coaxial wire has a proximal end, a proximal face, and a second longitudinal axis. The first longitudinal axis of the proximal core wire is aligned with the second longitudinal axis of the coaxial wire. The first material is then joined to the sleeve material at the distal face of the proximal core wire and the proximal face of the coaxial wire, with the first material not being joined directly to the core material. In some embodiments the first material is joined to the sleeve material through a weld. A distal portion of the sleeve material is then removed to expose the core material.

In some embodiments a distal segment of the proximal core wired may be shaped to have a tapered profile. The shaping may be done through the removal of material such as grinding. The first material may be stainless steel and the core material may be a nickel titanium alloy. The sleeve material may comprise a nickel alloy. In some embodiment the exposed portion of the distal core wire may be covered with a radiopaque material. The radiopaque material may be a platinum alloy wire wound about the distal core wire or a radiopaque jacket comprising a barium compounded thermoplastic covering the distal core wire. The proximal core wire may be coated with a lubricating coating. The lubricating coating may be a polytetrafluoroethylene coating or a hydrophilic material.

In another embodiment, a method for making a wire guide includes obtaining a proximal core wire and a distal core wire. The proximal core wire is comprised of a first material having a high modulus of elasticity and has a distal end, a distal face, a first outside diameter, and a first longitudinal axis. The distal core wire is comprised of a second material having a low modulus of elasticity and has a proximal end, a proximal face, a second outside diameter, and a second longitudinal axis. Material is removed from the distal face of the proximal core wire to form a cylindrical recess having an inside diameter complementary to the second outside diameter. The first longitudinal axis is aligned with the second longitudinal axis and the proximal end of the distal core wire is inserted into the recess. The proximal end of the distal core wire is then secured within the recess.

In some embodiments the proximal end of the distal core wire is secured within the recess through an interference fit. In other embodiments the distal core wire is secured within the recess through crimping the distal end of the proximal core wire. A distal portion of the proximal core wire may be shaped to have a tapered profile.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. A wire guide comprising:
  a proximal core wire comprised of a first material having a high modulus of elasticity, the proximal core wire having an outer surface, a distal end, a first outer diameter at the distal end, a first axis, a proximal core wire stiffness, and a transition segment proximate the distal end of the proximal core wire, the transition segment having an inward taper in a distal direction at a first section of the outer surface of the proximal core wire and an outward taper in the distal direction at a second section of the outer surface of the proximal core wire distal to the first section;
  a distal core wire comprised of a second material having a low modulus of elasticity, the distal core wire having a distal core wire length, a proximal end, a second axis, a distal core wire stiffness, and an outer surface, the second axis and the first axis being coaxial; and
  a sleeve secured about the proximal end of the distal core wire, the sleeve having a sleeve length less than the distal core wire length, an inner surface and a second outer diameter, the inner surface facing the outer surface of the distal core wire, the second outer diameter matching the first outer diameter, and the sleeve being joined to the distal end of the proximal core wire;
  wherein the proximal core wire stiffness proximal of the transition segment is greater than the distal core wire stiffness, the transition segment of the proximal core wire is entirely proximal to an interface between the proximal core wire and the distal core wire, and the transition segment reduces the proximal core wire stiffness to reduce a stress concentration at the interface between the proximal core wire and the distal core wire.

2. The wire guide of claim 1 wherein the sleeve consists of stainless steel and is welded to the distal end of the proximal core wire.

3. The wire guide of claim 1 wherein the first material is stainless steel, the second material is a nickel titanium alloy, and the sleeve is nickel.

4. A wire guide comprising:
  a proximal core wire comprised of a first material having a high modulus of elasticity, the proximal core wire having an outer surface, a distal end, a proximal core wire stiffness, a transition segment proximate the distal end of the proximal core wire, the transition segment having an inward taper in a distal direction at a first section of the outer surface of the proximal core wire and an outward taper in a distal direction at a second section of the outer surface of the proximal core wire distal to the first section, a cylindrical recess disposed at the distal end, and a first axis, the cylindrical recess having a recess inner surface; and
  a distal core wire comprised of a second material having a low modulus of elasticity, the distal core wire having a proximal end, a second axis, a distal core wire stiffness, and an outer surface, the proximal end of the distal core wire being secured within the cylindrical recess at the distal end of the proximal core wire with the recess inner surface facing the outer surface of the distal core wire;
  wherein the proximal core wire stiffness proximal of the transition segment is greater than the distal core wire stiffness, the transition segment of the proximal core wire is entirely proximal to an interface between the proximal core wire and the distal core wire, and the transition segment reduces the proximal core wire stiffness to reduce a stress concentration at the interface between the proximal core wire and the distal core wire.

5. The wire guide of claim 4 wherein the proximal end is secured within the recess through an inelastic deformation of the proximal core wire.

6. The wire guide of claim 4 wherein the first material is stainless steel and the second material is a nickel titanium alloy.

7. The wire guide of claim 1 wherein the first section of the outer surface of the proximal core wire is shorter in length than the second section of the outer surface of the proximal core wire.

8. The wire guide of claim 1 wherein the inward taper at the first section of the outer surface of the proximal core wire and the outward taper at the second section of the outer surface of the proximal core wire are curved.

9. The wire guide of claim 1 wherein the inward taper at the first section of the outer surface of the proximal core wire and the outward taper at the second section of the outer surface of the proximal core wire are generally straight.

10. The wire guide of claim 9 wherein the first section and the second section of the outer surface of the proximal core wire have about the same length.

11. The wire guide of claim 4 wherein the first section of the outer surface of the proximal core wire is shorter in length than the second section of the outer surface of the proximal core wire.

12. The wire guide of claim 4 wherein the inward taper at the first section of the outer surface of the proximal core wire and the outward taper at the second section of the outer surface of the proximal core wire are curved.

13. The wire guide of claim 4 wherein the inward taper at the first section of the outer surface of the proximal core wire and the outward taper at the second section of the outer surface of the proximal core wire are generally straight.

14. The wire guide of claim 13 wherein the first section and the second section of the outer surface of the proximal core wire have about the same length.

\* \* \* \* \*